United States Patent
Kreutz et al.

(10) Patent No.: US 11,332,494 B2
(45) Date of Patent: May 17, 2022

(54) NANOEMULSIONS AND METHODS FOR CANCER THERAPY

(71) Applicant: Fernando Thome Kreutz, Porto Alegre (BR)

(72) Inventors: Fernando Thome Kreutz, Porto Alegre (BR); Sergio Paulo Bydlowski, Sao Paulo (BR); Debora Levy, Sao Paulo (BR)

(73) Assignee: Fernando Thome Kreutz, Porto Alegre (BR)

( * ) Notice: Subject to any disclaimer, the term of this patent is extended or adjusted under 35 U.S.C. 154(b) by 0 days.

(21) Appl. No.: 16/097,515

(22) PCT Filed: Apr. 25, 2017

(86) PCT No.: PCT/IB2017/052378
§ 371 (c)(1),
(2) Date: Oct. 29, 2018

(87) PCT Pub. No.: WO2017/187343
PCT Pub. Date: Nov. 2, 2017

(65) Prior Publication Data
US 2019/0144492 A1 May 16, 2019

Related U.S. Application Data

(60) Provisional application No. 62/329,947, filed on Apr. 29, 2016.

(51) Int. Cl.
| | |
|---|---|
| *C07J 9/00* | (2006.01) |
| *C07J 71/00* | (2006.01) |
| *A61K 9/14* | (2006.01) |
| *A61K 31/575* | (2006.01) |
| *A61K 31/58* | (2006.01) |
| *A61K 45/06* | (2006.01) |
| *A61K 9/107* | (2006.01) |
| *C07J 11/00* | (2006.01) |

(52) U.S. Cl.
CPC ............ *C07J 9/005* (2013.01); *A61K 9/1075* (2013.01); *A61K 9/14* (2013.01); *A61K 31/575* (2013.01); *A61K 31/58* (2013.01); *A61K 45/06* (2013.01); *C07J 9/00* (2013.01); *C07J 11/00* (2013.01); *C07J 71/001* (2013.01)

(58) Field of Classification Search
CPC ..... C07J 9/005; C07J 9/00; C07J 11/00; C07J 71/001; A61K 9/1075; A61K 9/14; A61K 31/575; A61K 31/58; A61K 45/06
USPC ........................................................ 514/171
See application file for complete search history.

(56) References Cited

U.S. PATENT DOCUMENTS 5,578,583 A    11/1996    Maranhao

FOREIGN PATENT DOCUMENTS

| CA | 2861565  | 7/2013  |
| WO | 94/20145 | 9/1994  |
| WO | 01/93918 | 12/2001 |

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Prete et al., Evaluation in melanoma-bearing mice of an etoposide derivative associated to a cholesterol-rich nanoemulsion, 2006, JPP, 58, 801-808 (Year: 2006).*
Junping et al., Pharmacokinetics and antitumor effects of vincristine carried by microemulsions composed of PEG-lipid, oleic acid, vitamin E and cholesterol, 2003, International Journal of Pharmaceutics, 251, 13-21 (Year: 2003).*
Zhang et al., A dual-targeting drug co-delivery system for tumor chemo- and gene combined therapy, 2016, Materials Science and Engineering C, 64, 208-218 (Year: 2016).*
Carvalho et al. "Sterols as Anticancer Agents: Synthesis of Ring-B Oxygenated Steroids, Cytotoxic Profile, and Comprehensive SAR Analysis" Journal of Medicinal Chemistry, 53:7632-7638 (2010).
Carvalho et al. "Selective Cytotokicity of Oxysterols through Structural Modulation on Rings A and B. Synthesis, in Vitro Evaluation, and SAR" Journal of Medicinal Chemistry, 54(18):6375-6393 (2011) (Abstract only).
Favero et al. "Synthetic nanoemulsion resembling a protein-free model of 7-ketocholesterol containing low density Tipoprotein: In vitro and in vivo studies" Biological Research, 43:439-444 (2010).
International Search Report and the Written Opinion of the International Searching Authority corresponding to International Patent Application No. PCT/IB2017/052378 (9 pages) dated Oct. 17, 2017).
Salvador et al. "Anticancer steroids: linking natural and semi-synthetic compounds" Natural Product Reports, 30(2):324-374 (2013) (Abstract only).

\* cited by examiner

*Primary Examiner* — Kristin A Vajda
(74) *Attorney, Agent, or Firm* — Myers Bigel, P.A.

(57) ABSTRACT

An oxysterol or oxysterol-like compound is provided, which finds use in treating and/or targeting cancer.

6 Claims, 18 Drawing Sheets

NANOEMULSIONS AND METHODS FOR CANCER THERAPY

FIELD

The present invention relates to oxysterols. More specifically, the present invention is, in aspects, concerned with oxysterols, compositions comprising the oxysterols, and methods for the treatment of cancer.

BACKGROUND

Certain oxysterols are known to be cytotoxic. For example, Favero et al. (*Biol Res* 43:439-444, 2010) describes the preparation of a nanoemulsion comprising the oxysterol 7-ketocholesterol (7-KC) and describes the cytotoxic effects of oxidized LDL, which have been widely attributed to bioactive compounds like oxysterols such as 7-KC.

Additionally, cholesterol microemulsions carrying chemotherapeutic molecules have been used to target cancer cells that have increased LDL receptor expression on their cell surface. For example, U.S. Pat. No. 5,578,583 describes that microemulsions, similar in chemical composition to the lipid portion of low density lipoprotein (LDL), but not containing the protein portion, can be used as vehicles for the delivery of chemotherapeutic or diagnostic agents to neoplastic cells, while avoiding normal cells. When these artificial microemulsion particles are injected in the blood stream or incubated with plasma, they incorporate plasma apolipoproteins on to their surface. The microemulsions can then be incorporated into cells via receptors for LDL and deliver molecules which are incorporated in the core or at the surface of the microemulsion.

There is a need for alternative therapies to overcome or mitigate at least some of the deficiencies of the prior art.

SUMMARY

In accordance with an aspect, there is provided a compound of Formula (I), (II) or (III):

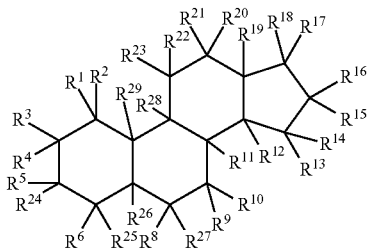

Formula (I)

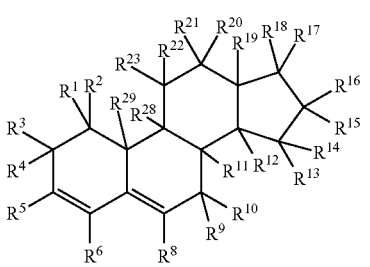

Formula (II)

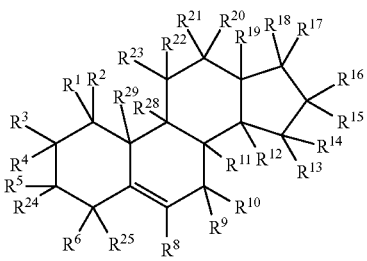

Formula (III)

wherein:
$R^1$ to $R^4$, $R^{11}$ to $R^{23}$, $R^{28}$ and $R^{29}$ are each independently selected from H, a substituted or unsubstituted hydrocarbon group;

$R^5$, $R^6$, $R^{24}$, and $R^{25}$ are each independently selected from H, a substituted or unsubstituted hydrocarbon group, a substituted or unsubstituted heterogeneous group;

$R^8$, $R^{26}$, and $R^{27}$ are each independently selected from H, a substituted or unsubstituted hydrocarbon group, or a substituted or unsubstituted heterogeneous group, or $R^{26}$ and $R^8$ or $R^{27}$ together form a substituted or unsubstituted carbocyclic group, or a substituted or unsubstituted heterocyclic group; and $R^9$ and $R^{10}$ are each independently selected from H, a substituted or unsubstituted hydrocarbon group, or a substituted or unsubstituted heterogeneous group, or $R^9$ and $R^{10}$ together form a carbonyl (=O) group;

and/or a pharmaceutically-acceptable salt, hydrate, solvate, tautomer, optical isomer, or combinations thereof.

In an aspect, $R^1$ to $R^4$, $R^{11}$ to $R^{23}$, $R^{28}$ and $R^{29}$ are each independently selected from H, a substituted or unsubstituted alkyl group, a substituted or unsubstituted alkenyl group, a substituted or unsubstituted alkynyl group.

In an aspect, $R^1$ to $R^4$, $R^{11}$ to $R^{23}$, $R^{28}$ and $R^{29}$ are each independently selected from H, a substituted or unsubstituted $C_1$-$C_{20}$ alkyl, a substituted or unsubstituted $C_2$-$C_{20}$ alkenyl, or a substituted or unsubstituted $C_2$-$C_{20}$ alkynyl.

In an aspect, $R^1$ to $R^4$, $R^{11}$ to $R^{23}$, $R^{28}$ and $R^{29}$ are each independently selected from H, a substituted or unsubstituted $C_1$-$C_{10}$ alkyl, a substituted or unsubstituted $C_2$-$C_{10}$ alkenyl, or a substituted or unsubstituted $C_2$-$C_{10}$ alkynyl.

In an aspect, $R^1$ to $R^4$, $R^1$ to $R^{16}$, $R^{18}$, $R^{20}$ to $R^{23}$ and $R^{28}$ are each H and $R^{17}$, $R^{19}$ and $R^{29}$ are each independently selected from a substituted or unsubstituted hydrocarbon group.

In an aspect, $R^5$, $R^6$, $R^{24}$, and $R^{25}$ are each independently selected from H, a hydroxyl group, a substituted or unsubstituted carboxyalkyl group.

In an aspect, the substituted or unsubstituted carboxyalkyl group is a substituted or unsubstituted R—C(=O)—O— and R is a substituted or unsubstituted hydrocarbon group.

In an aspect, $R^6$, $R^{24}$, and $R^{25}$ are H and $R^5$ is the substituted or unsubstituted carboxyalkyl group.

In an aspect, $R^8$, $R^{26}$, and $R^{27}$ are each independently selected from H or a hydroxyl group, or $R^{26}$ and $R^8$ or $R^{27}$ together form a substituted or unsubstituted heterocyclic group.

In an aspect, $R^8$, $R^{26}$, and $R^{27}$ are each independently selected from H or a hydroxyl group.

In an aspect, $R^8$ is selected from H or a hydroxyl group and $R^{26}$, and $R^{27}$ together form a substituted or unsubstituted heterocyclic group.

In an aspect, the substituted or unsubstituted heterocyclic group is an oxirane.

In an aspect, $R^9$ and $R^{10}$ are each independently selected from H, a substituted or unsubstituted hydrocarbon group.

In an aspect, $R^9$ and $R^{10}$ together form a carbonyl (=O) group.

In an aspect, the compound is selected from the group consisting of: 7-ketocholesterol; cholestane-3α-5β-6α-triol; 3,5-cholestadien-7-one; (3β,5α,6α)-cholestane-3,6-diol; cholesteryl acetate; 7-oxocholest-5-en-3-beta-yl acetate; 5β-6β-epoxy-cholesterol; and (3β,5α,6α)-3-Hydroxy-5,6-epoxycholestan-7-one.

In an aspect, the compound is assembled into lipoprotein-like particles.

In accordance with an aspect, there is provided a lipoprotein-like particle formed from one or more of the compounds described herein.

In an aspect, the lipoprotein-like particle described herein is carrying an agent.

In an aspect, the agent is a cancer therapeutic.

In an aspect, the compound and the agent exert a synergistic effect against cancer.

In accordance with an aspect, there is provided a composition comprising the compound described herein or the lipoprotein-like particle described herein.

In an aspect, the composition is in the form of an emulsion.

In an aspect, the emulsion is a microemulsion.

In an aspect, the emulsion is a nanoemulsion.

In accordance with an aspect, there is provided a method of treating cancer, comprising administering the compound described herein, the lipoprotein-like particle described herein, or the composition described herein to a subject in need thereof.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION

Figure 1:
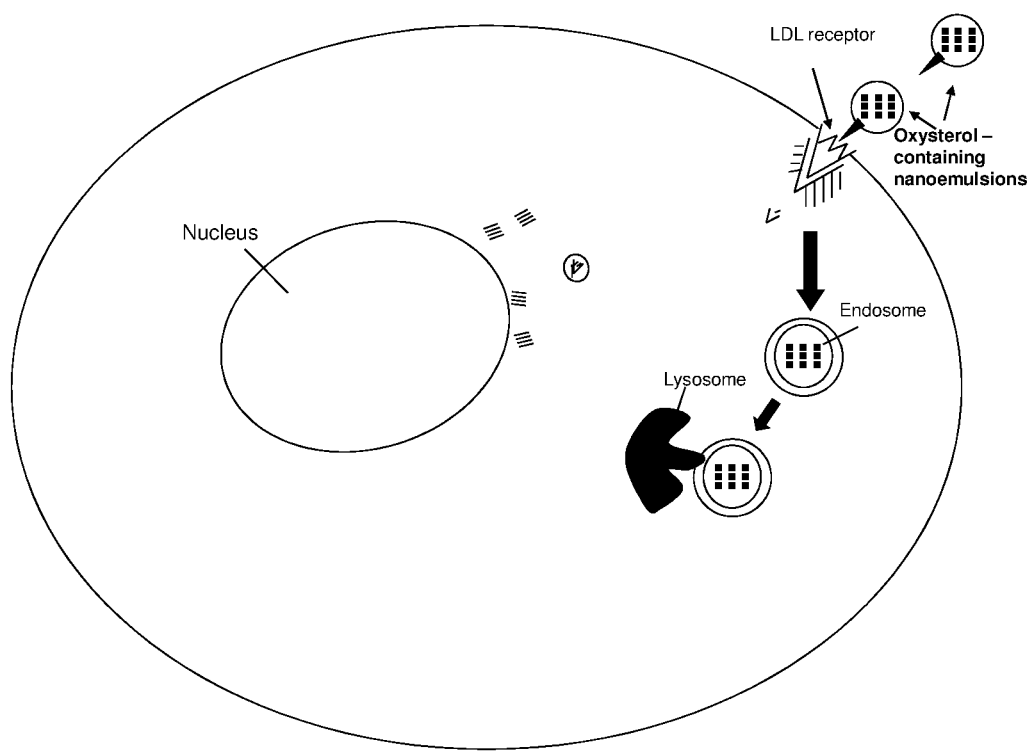
FIG. 1 is a schematic showing how it is believed that oxysterol-containing nanoemulsions bind to the low density lipoprotein receptor (LDLr) and internalized into a cancer cell, where the oxysterols are free to act as promoters of cell death.

Although certain oxysterols are known to be cytotoxic, it has now been found that oxysterols are particularly useful in cancer treatment and/or prevention. Furthermore, while native cholesterol has been used previously to form microemulsions in which cancer therapeutics could be carried and targeted to LDL receptor-expressing cancer cells, it has now been found that micro and nanoemulsions made with oxysterols can be delivered preferentially to cancer cells where they will act, alone or together with a therapeutic they may be carrying. In this way, there is, in an aspect, an unexpected synergistic effect with respect to cancer treatment: the oxysterol targets cancer cells that tend to express high levels of LDL receptors and itself exerts a cytotoxic effect on those cells and also improves targeted delivery of a cancer therapeutic.

Definitions

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder such as cancer, or may render the cells more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat cancer. Effective amounts of the compounds described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The compounds described herein may, in aspects, be administered before, during or after treatment with conventional therapies for the disease or disorder in question, such as cancer.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

The compounds of the present invention may have asymmetric centers, chiral axes, and chiral planes (as described, for example, in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, E isomers, and Z isomers, being included in the present invention. In addition, the compounds disclosed herein may exist as tautomers and both tautomeric forms are intended to be encompassed by the scope of the invention, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C=O)—O—.

The term "carbonyl group", whether used alone or with other terms, such as "aminocarbonyl group", denotes —(C=O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N, N-dimethyl-aminoethyl, N, N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl.

The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The present invention includes pharmaceutically acceptable salts, solvates and prodrugs of the compounds of the invention and mixtures thereof.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. For example, in aspects, the use of 7-KC is explicitly excluded from the compositions and methods described herein.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Oxysterols/Oxysterol-Like Compounds

It will be understood that any suitable oxysterol or oxysterol-like compound may be used in the emulsions, compositions, methods, and uses described herein. For example, in typical aspects, the oxysterol is a compound of general Formula (I), (II), or (III):

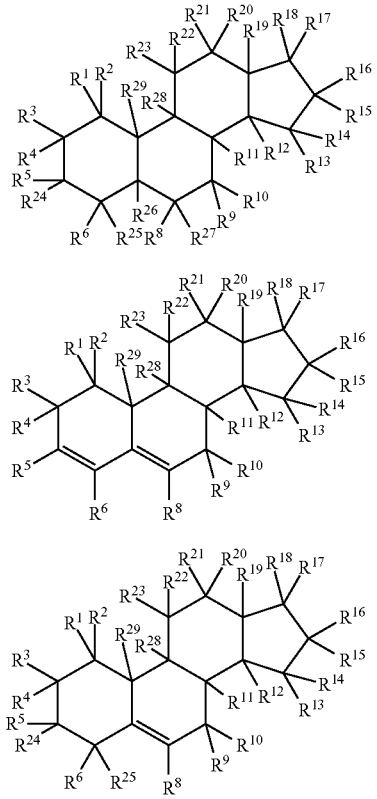

Formula (I)

Formula (II)

Formula (III)

wherein:
$R^1$ to $R^4$, $R^{11}$ to $R^{23}$, $R^{28}$ and $R^{29}$ are each independently selected from H, a substituted or unsubstituted hydrocarbon group;
$R^5$, $R^6$, $R^{24}$, and $R^{25}$ are each independently selected from H, a substituted or unsubstituted hydrocarbon group, a substituted or unsubstituted heterogeneous group;
$R^8$, $R^{26}$, and $R^{27}$ are each independently selected from H, a substituted or unsubstituted hydrocarbon group, or a substituted or unsubstituted heterogeneous group, or $R^{26}$ and $R^8$ or $R^{27}$ together form a substituted or unsubstituted carbocyclic group, or a substituted or unsubstituted heterocyclic group; and
$R^9$ and $R^{10}$ are each independently selected from H, a substituted or unsubstituted hydrocarbon group, or a substituted or unsubstituted heterogeneous group, or $R^9$ and $R^{10}$ together form a carbonyl (=O) group;
and/or a pharmaceutically-acceptable salt, hydrate, solvate, tautomer, optical isomer, or combinations thereof.

In aspects, $R^1$ to $R^4$, $R^{11}$ to $R^{23}$, $R^{28}$ and $R^{29}$ are each independently selected from H, a substituted or unsubstituted alkyl group, a substituted or unsubstituted alkenyl group, a substituted or unsubstituted alkynyl group. In typical aspects, $R^1$ to $R^4$, $R^{11}$ to $R^{23}$, $R^{28}$ and $R^{29}$ are each independently selected from H, a substituted or unsubstituted $C_1$-$C_{20}$ alkyl, a substituted or unsubstituted $C_2$-$C_{20}$ alkenyl, or a substituted or unsubstituted $C_2$-$C_{20}$ alkynyl. In typical aspects, $R^1$ to $R^4$, $R^{11}$ to $R^{23}$, $R^{28}$ and $R^{29}$ are each independently selected from H, a substituted or unsubstituted $C_1$-$C_{10}$ alkyl, a substituted or unsubstituted $C_2$-$C_{10}$ alkenyl, or a substituted or unsubstituted $C_2$-$C_{10}$ alkynyl.

In other aspects, $R^1$ to $R^4$, $R^{11}$ to $R^{16}$, $R^{18}$, $R^{20}$ to $R^{23}$ and $R^{28}$ are each H and $R^{17}$, $R^{19}$ and $R^{29}$ are each independently selected from a substituted or unsubstituted hydrocarbon group.

In other aspects, $R^5$, $R^6$, $R^{24}$, and $R^{25}$ are each independently selected from H, a hydroxyl group, a substituted or unsubstituted carboxyalkyl group. In typical aspects, the substituted or unsubstituted carboxyalkyl group is a substituted or unsubstituted R—C(=O)—O— and R is a substituted or unsubstituted hydrocarbon group. In other typical aspects, $R^6$, $R^{24}$, and $R^{25}$ are H and $R^5$ is the substituted or unsubstituted carboxyalkyl group.

In other aspects, $R^8$, $R^{26}$, and $R^{27}$ are each independently selected from H or a hydroxyl group, or $R^{26}$ and $R^8$ or $R^{27}$ together form a substituted or unsubstituted heterocyclic group. In typical aspects, $R^8$, $R^{26}$, and $R^{27}$ are each independently selected from H or a hydroxyl group. Typically, $R^8$ is selected from H or a hydroxyl group and $R^{26}$, and $R^{27}$ together form a substituted or unsubstituted heterocyclic group. Typically, the substituted or unsubstituted heterocyclic group is an oxirane.

In other aspects, $R^9$ and $R^{10}$ are each independently selected from H, a substituted or unsubstituted hydrocarbon group.

In other aspects, $R^9$ and $R^{10}$ together form a carbonyl (=O) group.

In typical aspects, the oxysterol or oxysterol-like compound is selected from one or a combination of the following compounds: 7-ketocholesterol; cholestane-3α-5β-6α-triol; 3,5-cholestadien-7-one; (3β,5α,6α)-cholestane-3,6-diol; cholesteryl acetate; 7-oxocholest-5-en-3-beta-yl acetate; 5β-6β-epoxy-cholesterol; and (3β,5α,6α)-3-Hydroxy-5,6-epoxycholestan-7-one.

It will be understood that the compounds described herein exist in different stereoisomeric forms and, while one stereoisomer may be described herein all stereoisomers are explicitly included herein, provided they are capable of emulsification and/or carrying an agent and/or targeting a cancer cell expressing an LDL receptor and/or they are cytotoxic.

The oxysterols described herein in aspects self-assemble into lipoprotein-like particles. The particles have a core that can be used to carry an additional agent, such as a cancer therapeutic. In this way, the oxysterol particles can be used to preferentially target the cancer therapeutic to a cancer cell, as cancer cells often upregulate expression of LDL receptors, to which the oxysterol particles will bind. Thus, in an aspect, the oxysterol and the cancer therapeutic will synergistically target and treat the cancer cells.

In an aspect, the oxysterols and oxysterol-like compounds described herein are made in accordance with the methods described in Carvalho, et al. (*J Med Chem* 2011, 54:6375-6393) and/or Salvador et al. (*Nat Prod Rep*, 2013, 30:324-374). Exemplary synthesis methods are shown in the Examples below.

Compositions Comprising Oxysterols

The oxysterols described herein, in aspects, are formulated into compositions. In typical aspects, the compositions are emulsions, such as microemulsions and nanoemulsions, typically nanoemulsions. In aspects, the oxysterols are emulsified using various methods and additional components. In typical aspects, the compositions are formulated as described, for example, in Favero et al. (*Biol Res* 43:439-444, 2010), incorporated by reference herein in its entirety.

The compositions and emulsions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions may include, albeit not exclusively, the oxysterols in association with one or more pharmaceutically acceptable vehicles or diluents, and may be contained in buffered solutions with a suitable pH that are iso-osmotic with physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of the subject. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example, but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesylphosphotidyl-ethanolamine (DOPE), and liposomes. Such compositions should contain a therapeutically effective amount of the modified cancer cells, together with a suitable amount of carrier so as to provide the form for direct administration to the patient.

Methods of Treatment

Unexpectedly, it has been found that oxysterols are useful for specifically targeting cancer cells that upregulate LDL receptors. Furthermore, oxysterols can assemble into lipoprotein-like particles that carry an additional agent, such as a cancer therapeutic, so that the oxysterol can be used as a targeting moiety to direct the cancer therapeutic to a cancer cell, as cancer cells tend to upregulate LDL receptors, to which the particles in the emulsion bind.

It has also been unexpectedly found that oxysterols are particularly cytotoxic to cancer cells. In aspects, oxysterols exhibit a higher cytotoxicity to cancer cells than to normal cells, at least in part due to the increased expression of LDL receptors on the surface of certain cancer cells.

In other aspects, it has unexpectedly been found that oxysterols and cancer therapeutics, administered in combination, exert a synergistic cytotoxic effect on cancer cells and can therefore be used to treat cancer in synergistic combination.

The cancer to be treated may be any type of malignancy and, in an aspect, is lung cancer, including small cell lung cancer and non-small cell lung cancer (e.g. adenocarcinoma), pancreatic cancer, colon cancer (e.g. colorectal carcinoma, such as, for example, colon adenocarcinoma and colon adenoma), oesophageal cancer, oral squamous carcinoma, tongue carcinoma, gastric carcinoma, liver cancer, nasopharyngeal cancer, hematopoietic tumours of lymphoid lineage (e.g. acute lymphocytic leukemia, B-cell lymphoma, Burkitt's lymphoma), non-Hodgkin's lymphoma (e.g. mantle cell lymphoma), Hodgkin's disease, myeloid leukemia (for example, acute myelogenous leukemia (AML) or chronic myelogenous leukemia (CML)), acute lymphoblastic leukemia, chronic lymphocytic leukemia (CLL), thyroid follicular cancer, myelodysplastic syndrome (MDS), tumours of mesenchymal origin, soft tissue sarcoma, liposarcoma, gastrointestinal stromal sarcoma, malignant peripheral nerve sheath tumour (MPNST), Ewing sarcoma, leiomyosarcoma, mesenchymal chondrosarcoma, lymphosarcoma, fibrosarcoma, rhabdomyosarcoma, melanoma, teratocarcinoma, neuroblastoma, brain tumours, medulloblastoma, glioma, benign tumour of the skin (e.g. keratoacanthoma), breast carcinoma (e.g. advanced breast cancer), kidney carcinoma, nephroblastoma, ovary carcinoma, cervical carcinoma, endometrial carcinoma, bladder carcinoma, prostate cancer, including advanced disease and hormone refractory prostate cancer, testicular cancer, osteosarcoma, head and neck cancer, epidermal carcinoma, multiple myeloma (e.g. refractory multiple myeloma), or mesothelioma. In an aspect, the cancer cells are derived from a solid tumour. Typically, the cancer cells are derived from a breast cancer, colorectal cancer, melanoma, ovarian cancer, pancreatic cancer, gastric cancer, lung cancer, or prostate cancer. More typically, the cancer cells are derived from a prostate cancer, a lung cancer, a breast cancer, or a melanoma. In typical aspects, the cancer cells express higher levels of the LDL receptor on their cell surface than normal cells of the same type.

The compositions of the invention can, in aspects, be administered for example, by parenteral, intravenous, subcutaneous, intradermal, intramuscular, intracranial, intraorbital, ophthalmic, intraventricular, intracapsular, intraspinal, intracisternal, intraperitoneal, intranasal, intrarectal, aerosol or oral administration. Typically, the compositions of the invention are administered subcutaneously, intramuscularly, or intradermally. More typically, the compositions of the invention are administered intradermally in the upper limbs due to the specific antigen processing that occurs in the derma.

The compositions of the invention may, in aspects, be administered in combination, concurrently or sequentially, with conventional treatments for cancer, including chemotherapy, hormone therapy, biotherapy, and radiation therapy, for example. The compositions of the invention may be formulated together with such conventional treatments when appropriate. In a specific aspect, the compositions of the invention may be administered in combination with the autologous cancer cell vaccine described in Canadian Patent Application No. 2,861,565, incorporated herein by reference.

The compositions of the invention may be used in any suitable amount, but are typically provided in doses comprising from about 0.1 µM to about 1000 µM oxysterol, such as from about 4 µM to about 60 µM oxysterol.

Additionally, treatment with the compositions described herein may occur once or may be repeated several times. For example, treatment may occur daily, weekly, monthly, yearly, or a combination thereof, depending upon the disease state. For example, a subject may be administered several doses on a weekly basis in order to treat an active cancer. Once the cancer growth slows or goes into remission, follow-up maintenance doses may be provided, for example, on a monthly basis, every three months, every six months, or on a yearly basis. Additionally, cancer patients are typically followed for several years after remission in order to quickly identify any signs of cancer relapse. If any such signs are identified, a follow-up dose or doses of the compositions described herein may be administered as needed to treat the relapsing cancer.

While it has been stated above that the oxysterols, emulsions, compositions, and methods can be used to treat cancer, it will be understood that they could also be used to prevent cancer.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1—Synthesis of Acetylated Cholesterol (Compound I)

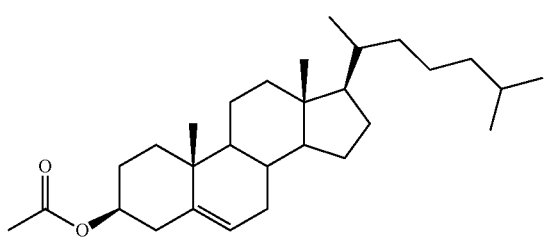 [SMILES: CC(=O)O[C@H]1CC[C@@]2(C)C(=CCC3C2CC[C@@]2(C)C3CC[C@@H]2C(C)CCCC(C)C)C1]

In a dry flask, THF (5 ml), cholesterol (3.87 g, 1.0 mmol), Ac$_2$O (11.2 mL, 100.0 mmol) and Bi(OTf)$_3$ (0.065 g, 0.1 mmol) were added and left under magnetic stirring at room temperature for 4 hours. Afterwards, the solution was poured into a separatory funnel, and ethyl acetate and NaHCO$_3$ (aq) were added and the organic and aqueous phases were separated. The aqueous phase was extracted three times with ethyl acetate, and then joined portions of the organic layer obtained was dried with MgSO$_4$, filtered and the solvent removed by evaporation at reduced pressure. Purification of the compound was carried out by recrystallization, and the obtained compound was dissolved in ethyl acetate:dichloromethane (10:1) to warm, leaving on standing, yielding the compound I.

Yield: 79%

Melting point: 107.1° C.

1H NMR data (300 MHz, CDCl3): δ=5.35 (d, J=4.4, 1H), 4.62 to 4.54 (m, 1H), 2.30 (d, J=7.2, 2H), 2.00 (s, 3H), 1.99 to 1.77 (m, 6H), 1.66 to 1.04 (m, 20H), 1, 00 (s, 3H), 0.90 (d, J=6.4, 3H), 0.85 (d, J=6.8, 3H), 0.84 (d, J=6, 8, 3H), 0.66 (s, 3H).

Example 2—Synthesis of Acetylated Oxidized Cholesterol (Compound II)

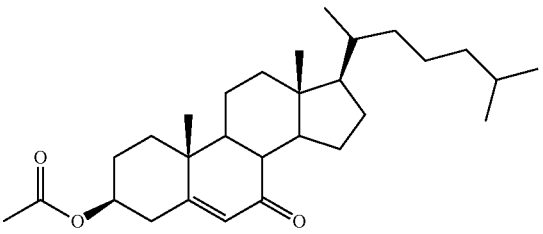 [SMILES: CC(=O)O[C@H]1CC[C@@]2(C)C(=CC(=O)C3C2CC[C@@]2(C)C3CC[C@@H]2C(C)CCCC(C)C)C1]

Acetylated oxidized cholesterol (compound II) was prepared in a solution with dichloromethane (11.5 mL) and acetylated cholesterol I (1 g, 2.3 mmol) in a flask, and then tert-hydroperoxide butyl (2.2 mL, 23 mmol), copper iodide (0.30 g, 1.564 mmol) and tetra-n-butylammonium fluoride (0.09 g, 0.276 mmol) were added. The reaction was condensed under reflux in a heating system (40° C.) for 24 hours and portions of tert-butyl hydroperoxide were added after an hour and a half and three hours of reaction. After the condensation, the solution was mixed with water containing crushed ice and poured into a separatory funnel, sequentially performing an extraction with dichloromethane. The organic and aqueous phases were separated and the organic phase was washed sequentially with 5% HCl, NaHSO$_3$ (aq) and distilled water, and after drying with NaSO$_4$. The solvent was removed by evaporation at reduced pressure. For purification of the compound a separation by column chromatography was carried out using silica as stationary phase and a mixture solvent of hexane:ethyl acetate in a ratio of 3:1 as mobile phase, yielding compound II.

Yield: 39%

Melting point: 156.2° C.

1H NMR data (300 MHz, CDCl3): δ=5.72 (s, 1H), 4.73 (m, 1H), 2:32 (m, 2H), 2.17 (m, 1H), 02.02 (m, 1H), 2.01, (s, 3H), 1.99 (s, 3H), 1.16 (s, 3H), 1.11 (s, 3H), 1.00 (s, 3H); 0.95 (s, 6H) ppm.

Example 3—Reduction of Acetylated Oxidized Cholesterol to Yield Compound III

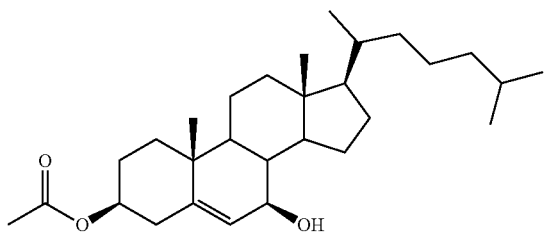 [SMILES: CC(=O)O[C@H]1CC[C@@]2(C)C(=C[C@H](O)C3C2CC[C@@]2(C)C3CC[C@@H]2C(C)CCCC(C)C)C1]

A solution was prepared with the acetylated oxidized cholesterol (compound II) of Example 2 (0.100 g, 0.22 mmol), $CeCl_3H_2O$ (0.247 g, 0.66 mmol) and a mixture of solvents THF:methanol (5,625 mL) with ratio of 5:1 in a flask. Then $NaBH_4$ (0.025 g, 0.66 mmol) was gradually added in small portions and the reaction was carried out under magnetic stirring and nitrogen atmosphere at room temperature for one hour. Then, the reaction was hydrolysed by addition of 10% HCl, the solution was poured into a separatory funnel and an extraction was performed with dichloromethane. The organic and aqueous phases were separated and the organic phase was dried with $MgSO_4$, filtered, and the solvent was removed by evaporation at reduced pressure. For purification of the compound recrystallization was carried out by dissolving the compound in methanol to hot, leaving on standing, yielding compound III.

Yield: 70%

Melting point: 104.7° C.

1H NMR data (300 MHz, CDCl3): δ=5.34 (s, 1H, 6-H), 4.61 (m, 1H, 3-H), 3.84 (d, J=8.0 Hz, 1H, 7-H), 2.03 (s, 3H, OAc), 1.06 (s, 3H, 19-H), 0.89 (d, J=6.3 Hz, 3H, H-21), 0.87 (d, J=6.6 Hz, 6H, 26-H, 27-H), 0.68 (s, 3H, 18-H) ppm.

Example 4—Deacetylation of Acetylated Oxidized Cholesterol to Yield Compound IV

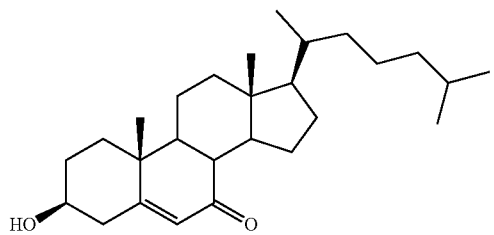

Chemical Formula: $C_{27}H_{44}O_2$
Exact Mass: 400.33

In a 50 ml flask, 1.13 mmol (0.5 g) of 3β-acetoxy-5-cholestan-7-one and NaOMe (0.5M in 1130 uL MeOH, 0.565 mmol) were added in a solution of 25 ml of chloroform and 15 ml of methanol. The reaction was stirred for 2 h. Dowex 50 was added for neutralization, and distilled water. After neutralization and filtering, the solvent was removed by reduced pressure. Purification was carried out using filtering column chromatography with hexane:ethyl acetate (1:1) to give compound IV.

Yield: 93%;

Melting point: 169-171° C.

1H NMR (300 MHz, CDCl3) δ ppm=5.68 (1H, d, J=1.7 Hz), 3.66 (1H, tt, J=10.7, 4.0 Hz), 1.19 (3H, s), 0.91 (3H, d, J=6.5 Hz), 0.85 (6H, 2d, J=6.6 Hz), 0.67 (3H, s).

Example 5—Cholesterol Oxidation to Yield Compound V

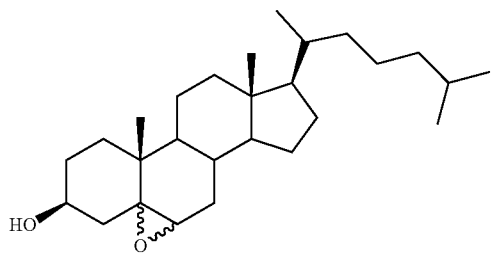

In a 50 ml flask, 0.52 mmol (0.2 g) of cholesterol dissolved in 20 ml of dichloromethane and 0.62 mmol (0,107 g) of m-chloroperbenzoic acid were added in small portions. The reaction was maintained under constant stirring and the progress of the reaction was checked by TLC. When no substrate was detected, the reaction was extracted with a 10% $NaHCO_3$ solution (3×30 mL) and washed with distilled water (2×30 mL). The organic phase was dried with $Na_2SO_4$, filtered and the solvent was removed under reduced pressure. For a filter Purification was column chromatography with a mixture hexane:ethyl acetate (1:1) to give compound V.

Yield: 57%

1H NMR (300 MHz, CDCl3) δ ppm=0.64 (3H, s), 0.86 and 0.87 (3H each), 0.89 (3H), 1.00 (3H, s), 2, 90 (1H, d, J=4.2 Hz), 3.96 to 3.85 (1H, m).

Example 6—Opening of Epoxidized Cholesterol to Yield Compound VI

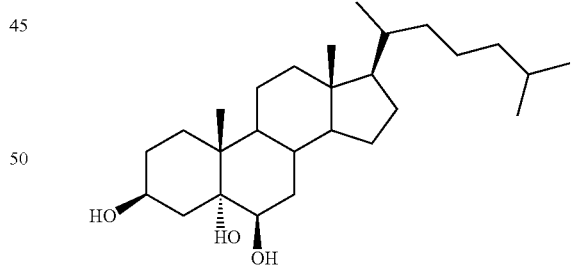

In a 50 mL balloon triplicate, 0.635 mmol (0.2556 g) of 5α,6α-epoxicolesteran-3β-ol dissolved in 10 ml of distilled water, and 10 mL of 1,4-dioxane were added. The reaction was stirred and reflux (105° C.), and was monitored by TLC. The reaction was extracted with EtOAc. The organic phase was dried with $Na_2SO_4$, filtered and the solvent was removed under reduced pressure. Filter purification was carried out using column chromatography with ethyl acetate: hexane (2:1) to give compound VI.

Yield: 50%;

Melting point: 247.5° C.;

1H NMR (300 MHz, CDCl3) δ ppm=0.68 (3H, s), 0.86 and 0.86 (each 3H, 2 d, J=6.6 Hz), 0.90 (3H, d, J=6.5 Hz), 1.18 (3H, s), 3.54 (1H, t, J=3.2 Hz), 4.10 (1H, tt, J=11 2, 5.5 Hz).

Example 7—Oxidation of Cholesterol to Yield Compound VII

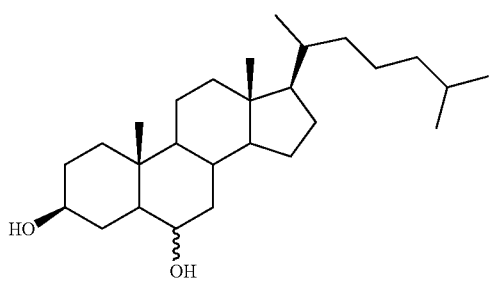 [SMILES: CC(C)CCCC(C)[C@H]1CCC2C3CC(O)C4C[C@@H](O)CC[C@]4(C)C3CC[C@@]21C]

A solution of 2.59 mmol (0.5 g) cholesterol in 30 mL cooled to 0° C. was added to a flask under inert atmosphere, then immediately placed in 15.5 mL of BH$_3$-THF complex, and stirred for 24 h at room temperature. The solution was cooled again to 0° C. and 15.5 ml 10% NaOH was added followed by 15.5 mL of 30% H$_2$O$_2$, leaving under stirring for a further 4 h. The mixture was neutralized with 5% HCl and the solvent was removed by reduced pressure. The aqueous phase was extracted with diethyl ether and 50 mL of 10% Na$_2$SO$_3$ was added to the organic phase. The solution was stirred for 2 h, the organic phase was washed with distilled water, dried with Na$_2$SO$_4$, filtered and evaporated. Purification was performed with column chromatography using hexane:ethyl acetate (2:1) as eluent, affording thus compound VII.

Yield: 40%;
Melting point: 150° C.

Example 8—Effects of Oxysterols and Oxysterol-Like Compounds on Cells Materials and Methods The purity of each oxysterol was determined to be 98% by GS/MS. For all experiments, a stock solution was prepared at a concentration of 1000 μM in absolute ethanol. The concentrations used in the experiments were in the range of those described to induce cell death on several cell lines. For the experiments, cells were plated at a density of 1.5×10$^3$ cells/cm$^3$ in triplicate in 96-well Black Flat Bottom Polystyrene Microplates (Corning, Mass.) and incubated in CO$_2$ atmosphere. Several concentrations of each oxysterol (0 to 100 μM, 200 μL final volume) were added to the media, followed by incubation for 24 h. At the end of this experimental period, several parameters were determined in each of the three samples, as described hereafter.

The oxysterol and oxysterol-like compounds used in the Examples herein are shown in Table 1, below:

TABLE 1

List of Exemplary Oxysterol and Oxysterol-Like Compounds

| | | |
|---|---|---|
| Ox-1 | 7-Ketocholesterol | 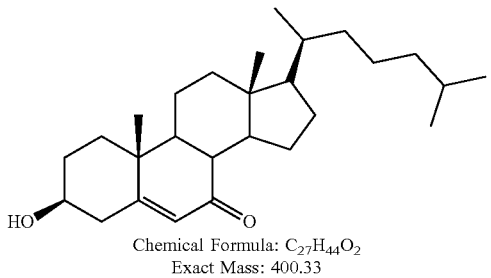<br>Chemical Formula: $C_{27}H_{44}O_2$<br>Exact Mass: 400.33 |
| Ox-2 | Cholestane-3α-5β-6α-triol | 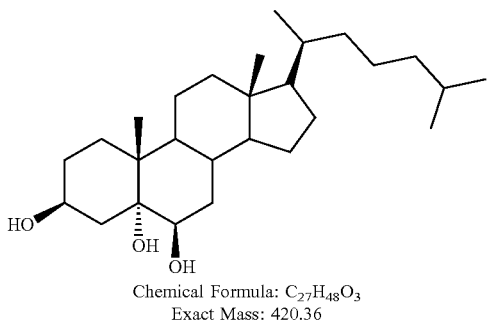<br>Chemical Formula: $C_{27}H_{48}O_3$<br>Exact Mass: 420.36 |
| Ox-3 | 3,5-cholestan-7-one | 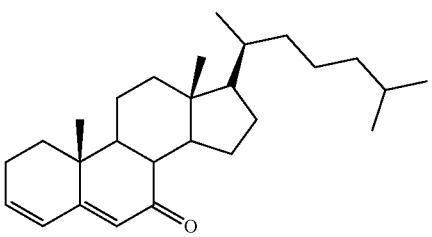 [SMILES: CC(C)CCC[C@H](C)C1CCC2C3C(=O)C=C4C=CCC[C@]4(C)C3CC[C@@]21C] |

TABLE 1-continued

List of Exemplary Oxysterol and Oxysterol-Like Compounds

Chemical Formula: C$_{27}$H$_{42}$O$_1$
Exact Mass: 382.62

Ox-4  (3α,5β,6α)-cholestane-3,6-diol

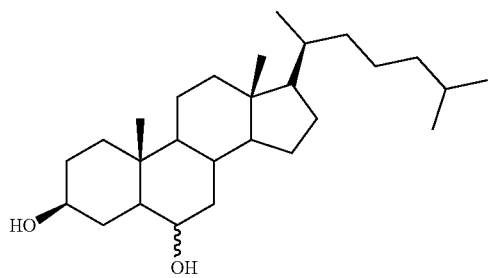 [SMILES: CC(C)CCC[C@H](C)C1CCC2C3CC(O)C4C[C@@H](O)CC[C@]4(C)C3CC[C@@]21C]

Chemical Formula: C$_{27}$H$_{48}$O$_2$
Exact Mass: 404.37

Ox-5  Cholesteryl acetate

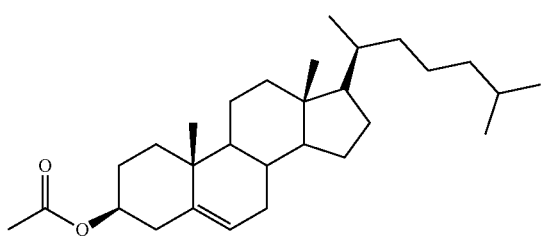 [SMILES: CC(=O)O[C@H]1CC[C@@]2(C)C(=CCC3C4CCC([C@@H](C)CCCC(C)C)[C@@]4(C)CCC32)C1]

Chemical Formula: C$_{29}$H$_{48}$O$_2$
Exact Mass: 428.37

Ox-6  7-oxocholest-5-en-3-β-yl acetate

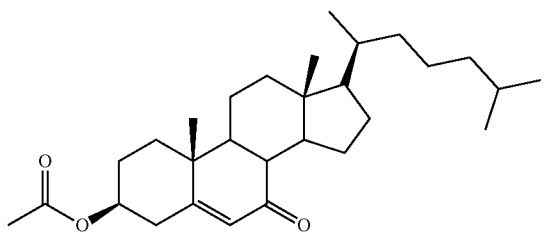 [SMILES: CC(=O)O[C@H]1CC[C@@]2(C)C(=CC(=O)C3C4CCC([C@@H](C)CCCC(C)C)[C@@]4(C)CCC32)C1]

Chemical Formula: C$_{29}$H$_{46}$O$_3$
Exact Mass: 442.34

Ox-7  5β-6β-epoxy-cholesterol

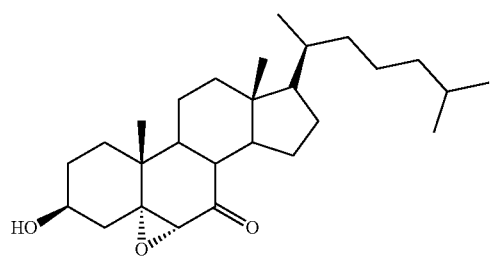 [SMILES: CC(C)CCC[C@H](C)C1CCC2C3C(=O)[C@@H]4O[C@@]45C[C@@H](O)CC[C@]5(C)C3CC[C@@]21C]

Chemical Formula: C$_{27}$H$_{44}$O$_3$
Exact Mass: 416.33

TABLE 1-continued

List of Exemplary Oxysterol and Oxysterol-Like Compounds

Ox-8    (3α,5β,6α)-3-OH-5,6-epoxycholestan-7-one

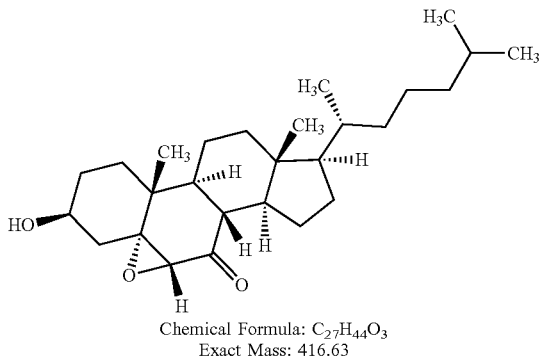

Chemical Formula: $C_{27}H_{44}O_3$
Exact Mass: 416.63

The cells used in the Examples herein are shown in Table 2, below:

TABLE 2

List of cells used in the experiments described below and select $IC_{50}$ values.

| Composto | Linhagem celular | | | | | | | | | |
|---|---|---|---|---|---|---|---|---|---|---|
| | MRC-5 $IC_{50}$ (μm) | Molt-4 $IC_{50}$ (μm) | Raji $IC_{50}$ (μm) | Jurkat $IC_{50}$ (μm) | PC-3 $IC_{50}$ (μm) | HepG-2 $IC_{50}$ (μm) | HeLa $IC_{50}$ (μm) | A172 $IC_{50}$ (μm) | T98G $IC_{50}$ (μm) | U87-MG $IC_{50}$ (μm) |
| Ox-1 | 78.6 | 38.0 | 63.3 | 55.8 | 19.2 | 42.5 | 33.2 | 15.6 | 0.0 | 55.6 |
| Ox-2 | 47.5 | 12.3 | 39.0 | 46.6 | 21.0 | 19.0 | 19.9 | 23.6 | 27.5 | 29.8 |

| | | |
|---|---|---|
| MRC-5 | ATCC CCL-171 | Human lung normal |
| Molt-4 | ATCC CRL-158 | Human Acute lymphoblastic leukemia |
| Raji | ATCC CCL-86 | Human Burkitt's lymphoblast |
| Jurkat | ATCC TIB-152 | Human Acute T cell leukemia |
| PC-3 | ATCC CRL-1435 | Human Prostate grade IV, adenocarcinoma |
| HepG-2 | ATCC HB-8065 | Human Hepatocellular carcinoma |
| HeLa | ATCC CCL-2 | Human Cervix adenocarcinoma |
| A172 | ATCC CRL-1620 | Human Brain glioblastoma |
| T98 | ATCC CRL-1690 | Human Brain glioblastoma |
| U87-MG | ATCC HTB-14 | Human Glioblastoma Astrocytoma |

Cell Viability Assay

Figure 2:
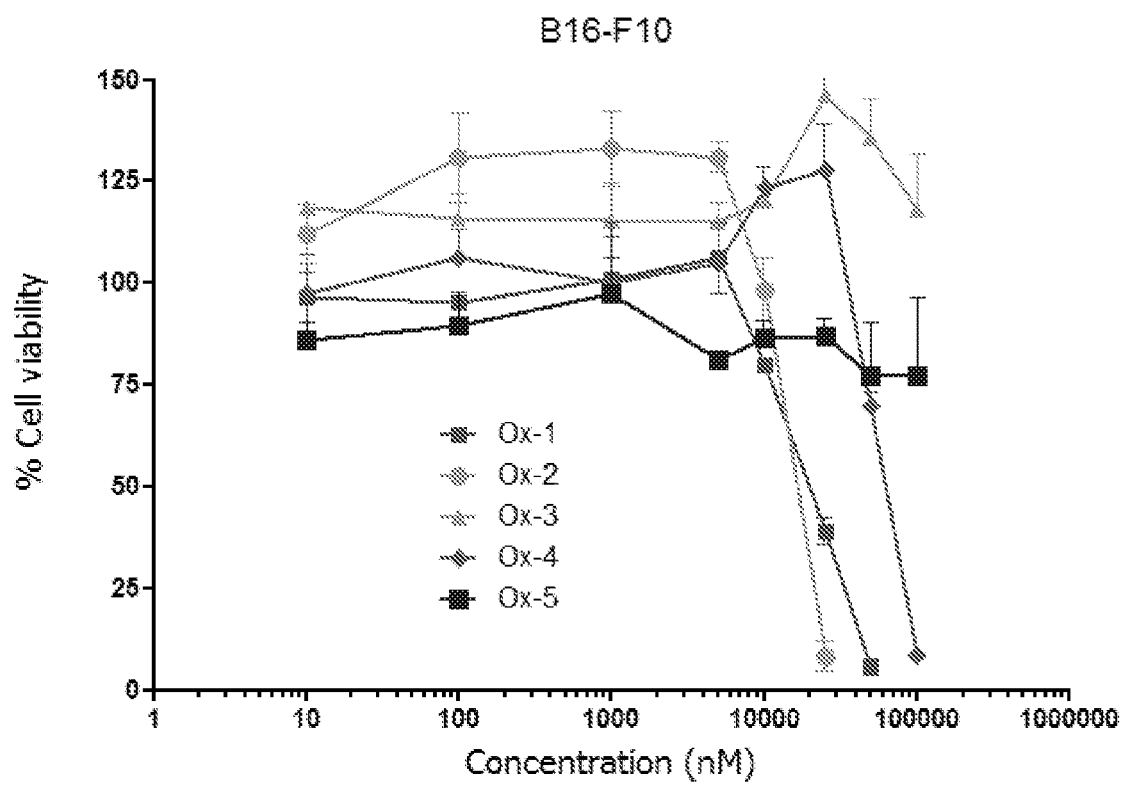
FIG. 2 shows dose response curves for Ox-1 through Ox5.

After 24 h cells were incubated with Hoechst 33342 (0.1 μg/mL) and 0.5 μl propidium iodide (PI) for 15 min. ImageXpress Micro high content screening system (Molecular Devices, Sunnyvale, Calif.) was used to determine the number of live and death cells. Nine sites per well and three wells per treatment were acquired. Cell Scoring MetaXpress software was used to analyze the number of cells and the viability. For $IC_{50}$ calculations, survival data were evaluated by variable slope curve-fitting with GraphPad Prism. Tables 3 and 4 show the $IC_{50}$ values for the tested compounds in different cell lines and FIG. 2 shows dose response curves for Ox-1 through Ox5.

TABLE 3

$IC_{50}$ values for Ox-1 through Ox-8 in MDA-MB-321 and B16-F10 cells.

| | MDA-MB-321 cell line $IC_{50}$ (uM) | | | B16-F10 cell line $IC_{50}$ (uM) | | |
|---|---|---|---|---|---|---|
| | 24 h | 48 h | 72 h | 24 h | 48 h | 72 h |
| Ox-1 | 54.4 | 50.4 | 48.1 | 19.9 | 21.7 | 29.6 |
| Ox-2 | 7.9 | 21.1 | 25.2 | 18.1 | 21.4 | 15.4 |
| Ox-3 | 0.0 | 0.0 | 0.0 | 0.0 | 376.7 | 52.9 |
| Ox-4 | 66.6 | 39.7 | 35.3 | 58.3 | 52.9 | 82.6 |
| Ox-5 | 0.0 | 0.0 | 89.8 | 0.0 | 0.0 | 0.0 |
| Ox-6 | 0.0 | 8564.8 | 828.8 | ND | ND | ND |

TABLE 3-continued

IC$_{50}$ values for Ox-1 through Ox-8 in MDA-MB-321 and B16-F10 cells.

| | MDA-MB-321 cell line IC$_{50}$ (uM) | | | B16-F10 cell line IC$_{50}$ (uM) | | |
|---|---|---|---|---|---|---|
| | 24 h | 48 h | 72 h | 24 h | 48 h | 72 h |
| Ox-7 | 58.8 | 52.5 | 60.3 | ND | ND | ND |
| Ox-8 | ND | ND | NO | ND | ND | ND |

TABLE 4

IC$_{50}$ values for Ox-1 through Ox-8 in different cells lines.

| | B16 F10 | MDA-MB-321 | LL 24 | HUV-EC |
|---|---|---|---|---|
| Oxi 1 | 35.6 | 37.6 | 49.5 | 39.4 |
| Oxi 2 | 41.3 | 37.5 | 38.4 | 73.6 |
| Oxi 3 | 117.5 | — | — | — |
| Oxi 4 | 42.4 | 59.0 | 28.3 | — |
| Oxi 5 | — | — | — | — |
| Oxi 6 | — | — | — | — |
| Oxi 7 | 78.3 | 84.6 | 66.0 | 84.8 |
| Oxi 8 | 37.0 | 40.0 | 46.5 | 35.2 |

Detection of Apoptosis and Necrosis

Figure 3A:
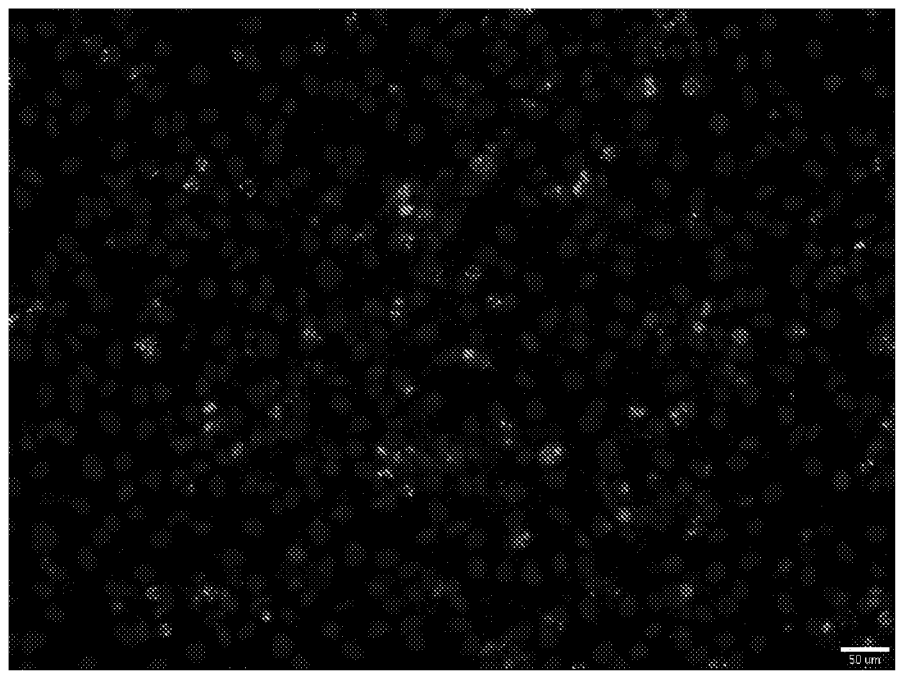
FIGS. 3A, 3B, and 3C show staining results indicating apoptotic B16 F10 cells.
Figure 3B:
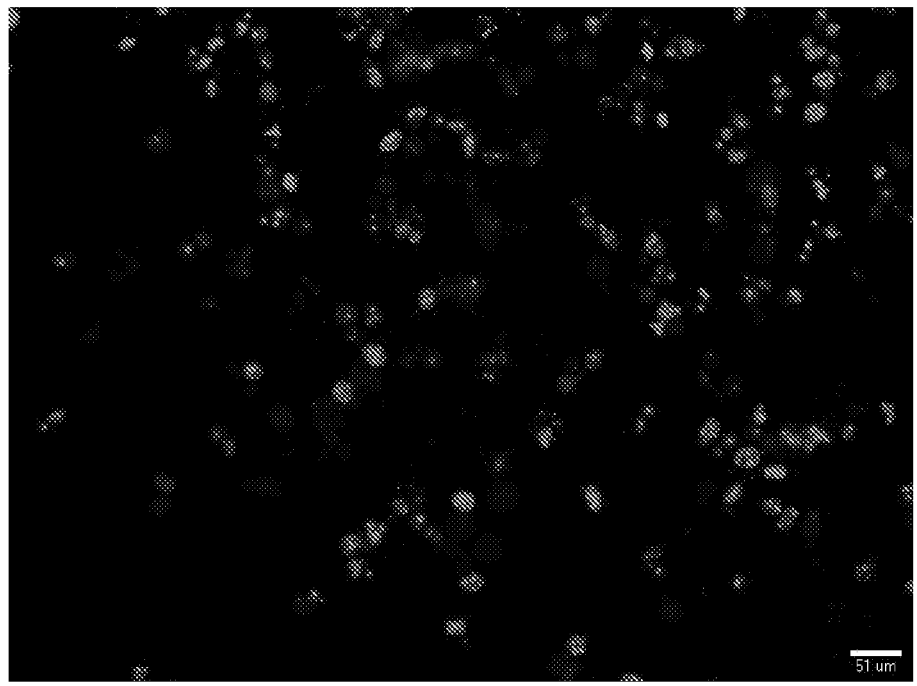
Figure 3C:
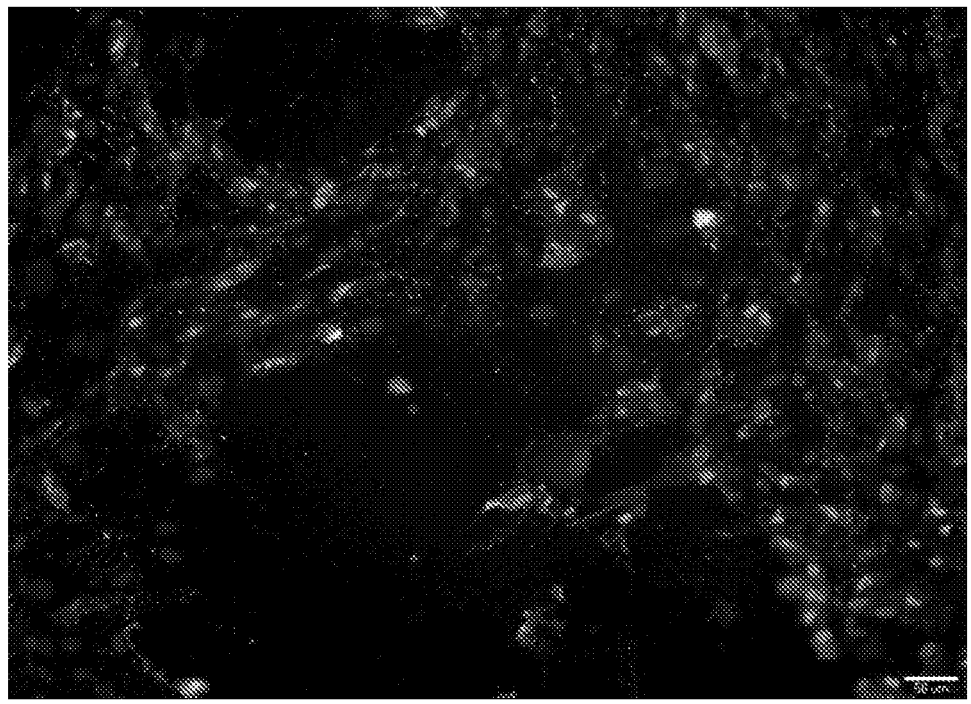
Figure 4A:
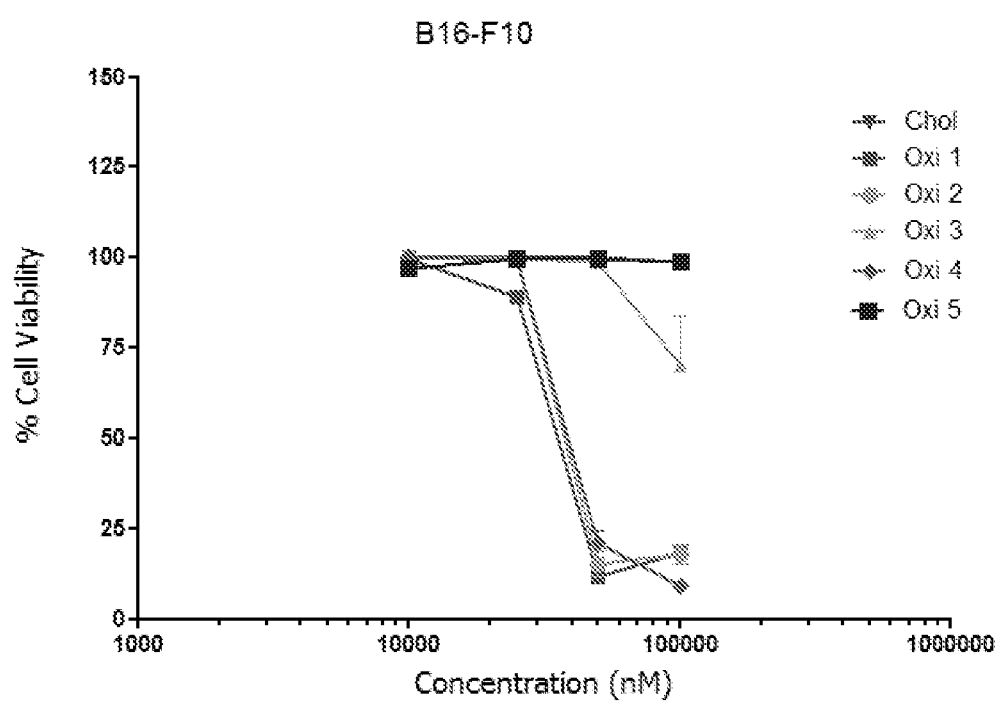
FIGS. 4A, 4B, and 4C show graphs relating to apoptotic B16 F10 cells.
Figure 4B:
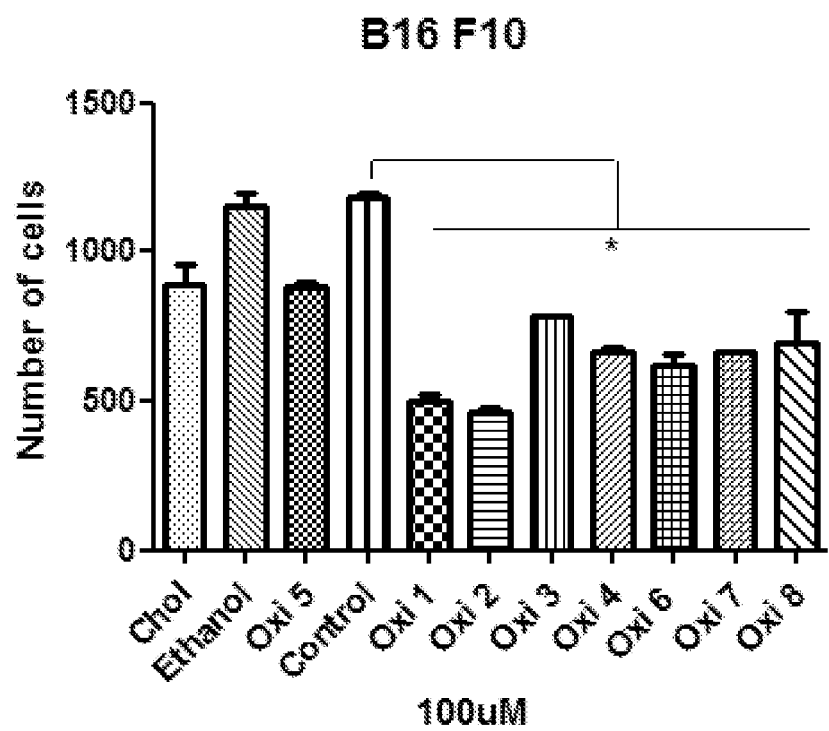
Figure 4C:
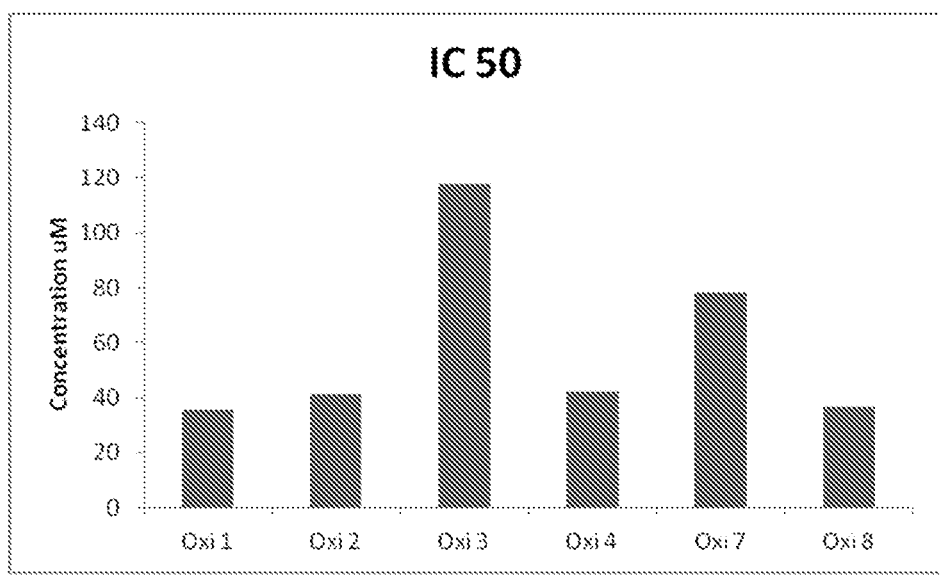
Figure 5A:
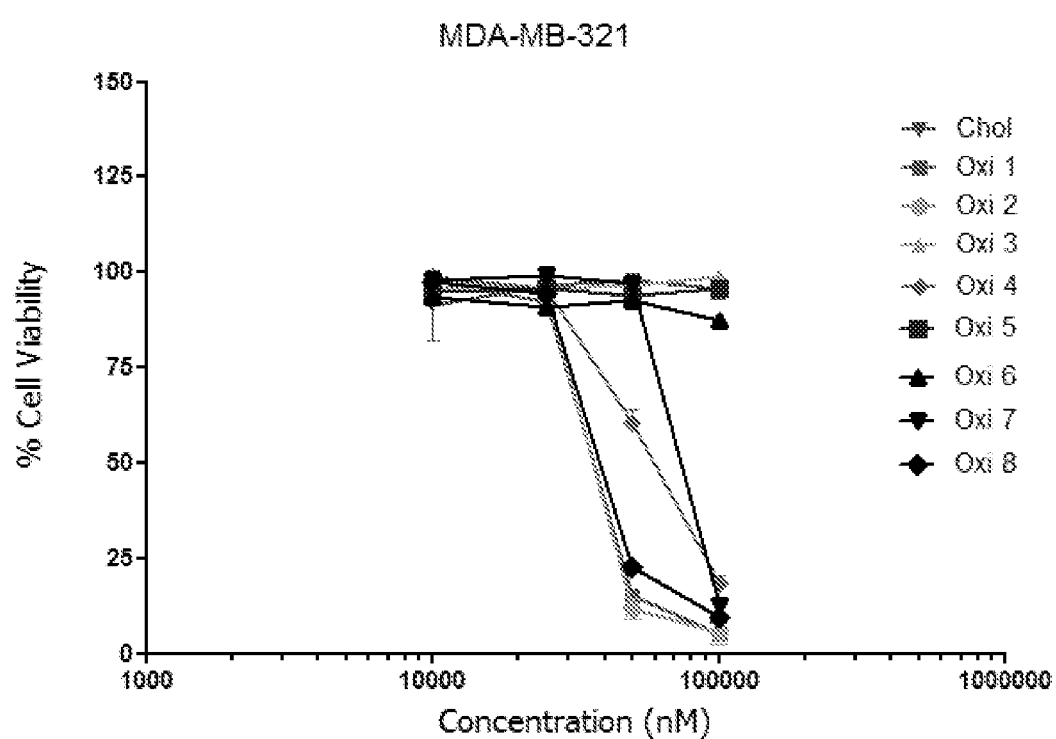
FIGS. 5A, 5B, and 5C show graphs relating to apoptotic MDA-MB-321 cells.
Figure 5B:
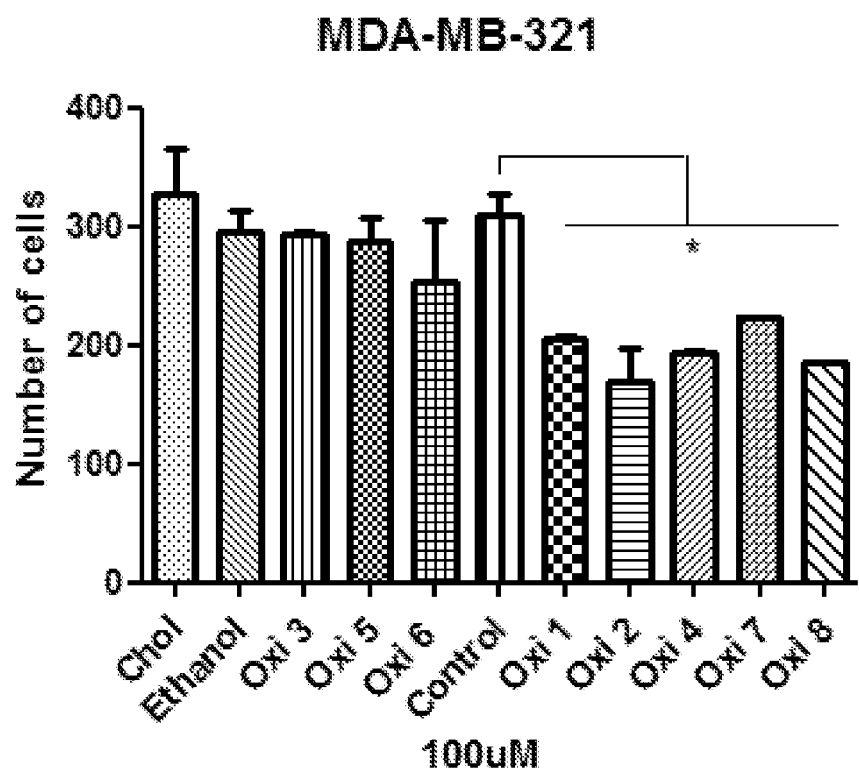
Figure 5C:
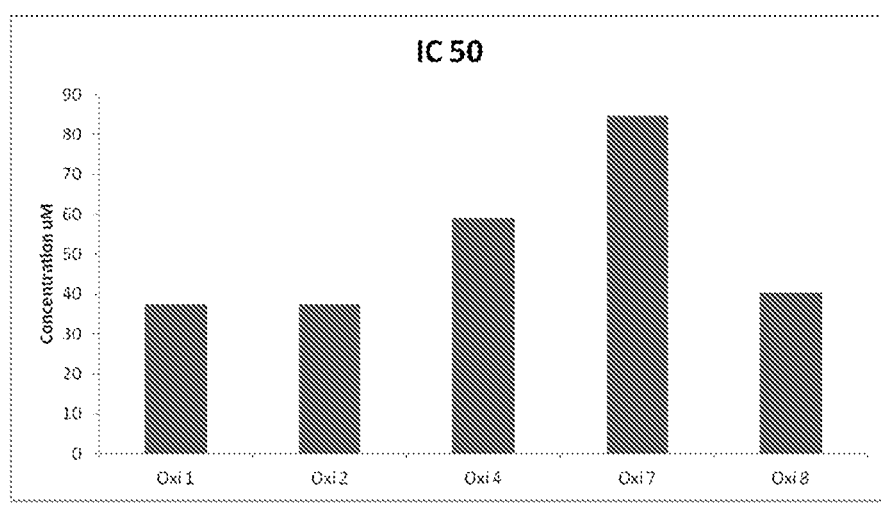
Figure 6A:
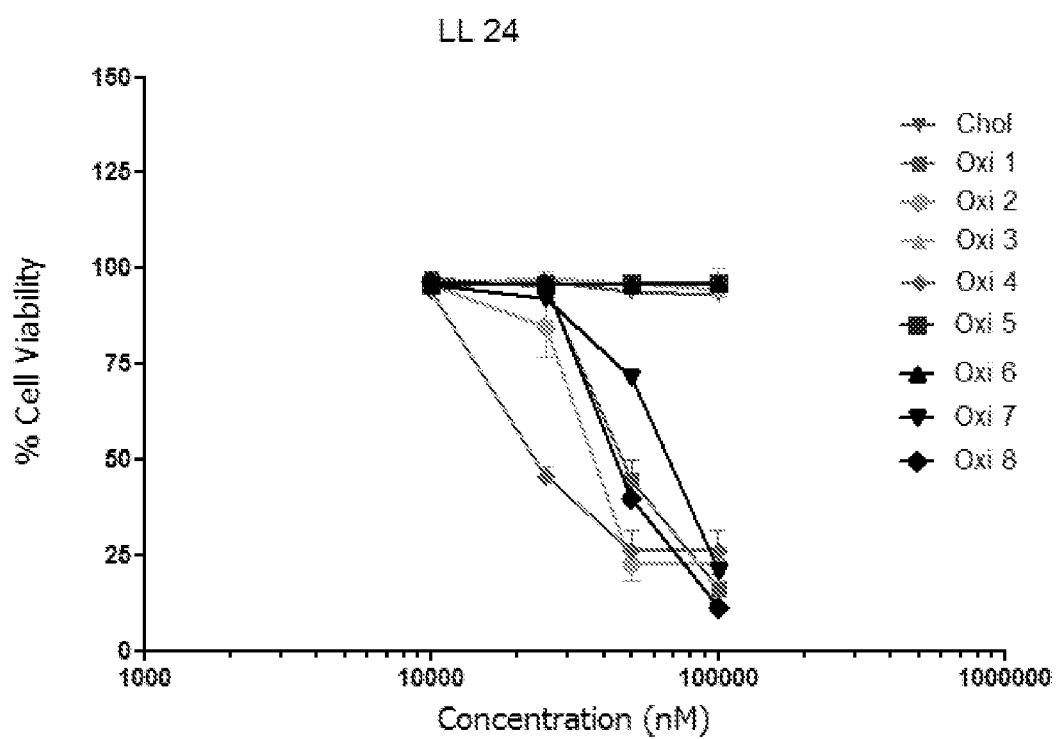
FIGS. 6A, 6B, and 6C show graphs relating to apoptotic LL 24 cells.
Figure 6B:
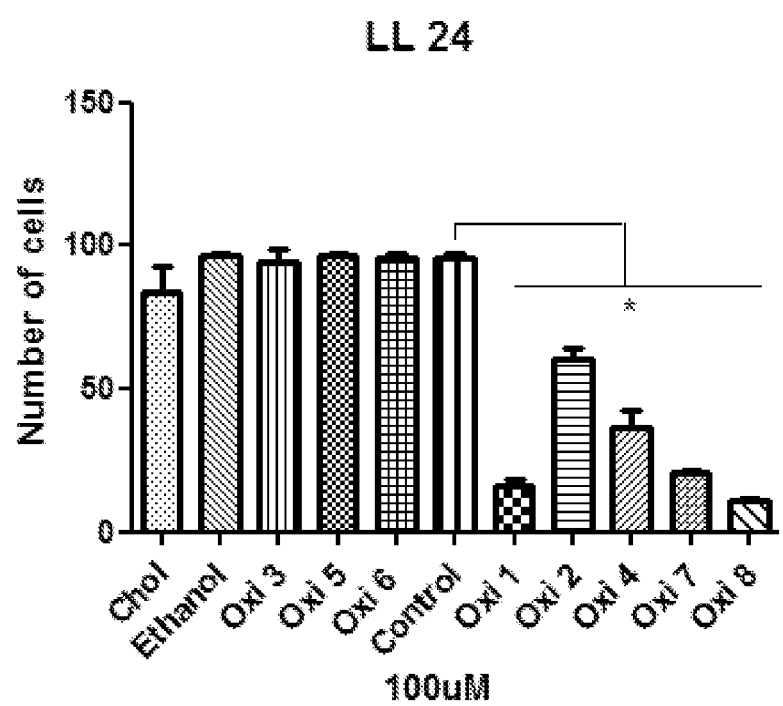
Figure 6C:
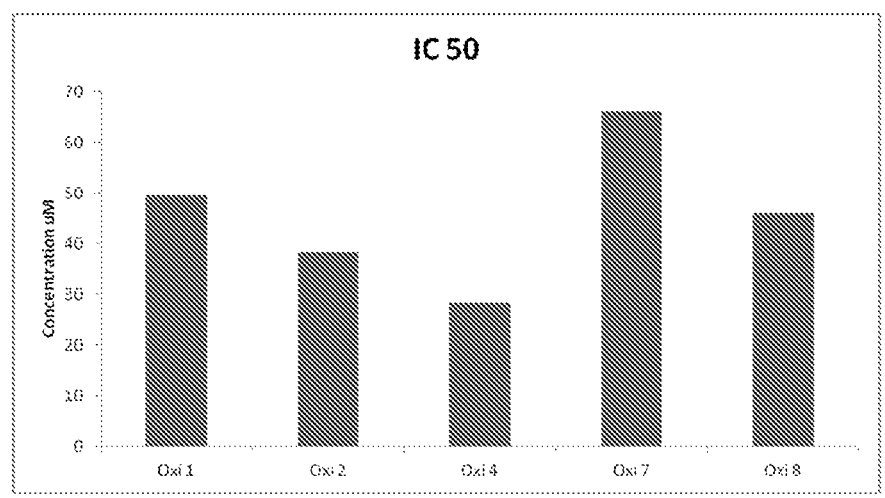

The Annexin V:FITC Apoptosis Detection Kit I (BD Biosciences) was used to determine the percentage of apoptotic cells, as described by the manufacturer. Cells were incubated with 0.5 µl of FITC Annexin V and 0.5 µl PI and incubated for 15 min at room temperature in the dark. The nuclei were counterstained with 0.1 µg/mL Hoechst 33342 (Molecular Probes, NY) for 10 min. The presence of apoptosis was analyzed within 1 h using an ImageXpress. Nine sites per well and three wells per treatment were acquired. Apoptosis (%) was determined by the MetaXpress Cell Health software application. Cells stained with Hoechst 33342 were considered as living cells. Apoptotic process was defined by the presence of annexin V or annexin V/PI. Cells stained only with PI were considered as necrotic cells. Staining results are shown in FIGS. 3A, 3B, and 3C (7-KC 50 µM in B16 F10 cells) and data are shown in FIGS. 4A, 4B, and 4C for B15 F10 cells; in FIGS. 5A, 5B, and 5C for MDA-MB-321 cells; and in FIGS. 6A, 6B, and 6C for LL 24 cells.

Detection of Caspase-3/7 Activity

Caspase-3/7 activity was measured using the NucView 488 Caspase-3 Assay kit for live cells (Biotium, Hayward, Calif.). The nuclei were counterstained with 0.1 µg/mL Hoechst 33342. Fluorogenic substrates were determined using ImageXpress. Nine sites per well and three wells per treatment were acquired. Caspase-3/7 activity was determined using the cell scoring MetaXpress software.

Detection of Autophagy

Autophagy was measured by the accumulation of the antibody LC3b in autophagosomes as result of the disruption in normal autophagic flux. LC3b Antibody Kit for Autophagy (Molecular Probes) was used as described in the manufacturer's protocol. The antibody was diluted 1:200 and 60 µM of chloroquine diphosphate was used as control of the autophagosome expression. The nuclei were counterstained with 0.1 µg/mL Hoechst 33342. The presence of the autophagosome were determined using ImageXpress. Nine sites per well and three wells per treatment were acquired. The percentage of autophagic cells was determined using the cell scoring MetaXpress software.

Measurement of Transmembrane Mitochondrial Potential (ΔΨ)

At the end of the experimental period, treated cells were incubated with 50 nM TMRE (Sigma-Aldrich, St Louis, Mo., USA) for 30 min at 37° C. TMRE is a potentiometric and cationic indicator die that accumulates preferentially in energized mitochondria Cell nuclei were counterstained with 0.1 µg/mL Hoechst 33342. TMRE fluorescence was determined using ImageXpress. Nine sites per well and three wells per treatment were acquired. Transmembrane mitochondrial potential was determined using the cell scoring MetaXpress software.

Cell Cycle Evaluation with Hoechst 33342

Figure 7:
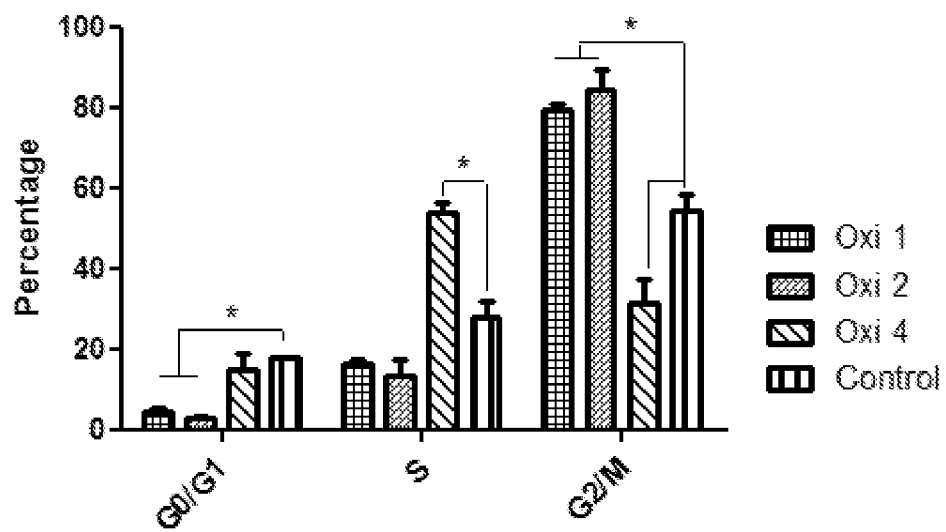
FIG. 7 shows cell cycle evaluation analysis after treatment with oxysterols.

Oxysterol-treated cells were fixed in a solution of 4% paraformaldehyde (Sigma-Aldrich) for 15 min. After washing twice with DPBS, the cells were incubated with Hoechst 33342 (0.1 µg/mL) for 15 min. ImageXpress was used to determine the cell cycle. Nine sites per well and three wells per treatment were acquired. Cell cycle MetaXpress software was used to analyze the different phases of the cell cycle. Results are shown in FIG. 7.

Changes in F-Actin Organization

Figure 8A:
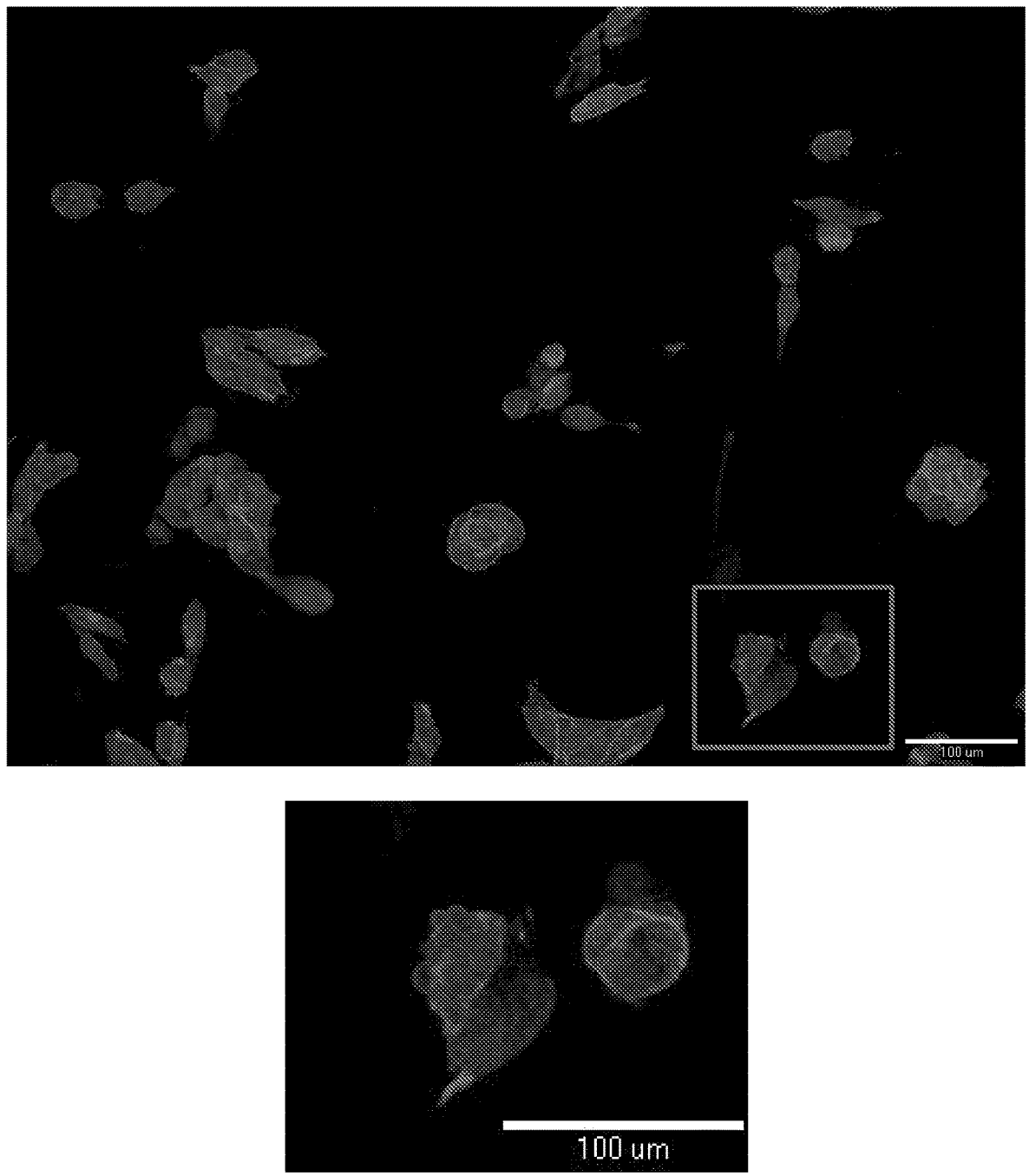
FIGS. 8A, 8B, and 8C show changes in F-actin organization after treatment with 7-KC in B16 F10 cells (8A), (3β,5α,6α)-3-Hydroxy-5,6-epoxycholestan-7-one in B16 F10 cells (8B), and 7 oxocholest-5-en-3-beta-yl acetate in B16 F10 cells (8C).
Figure 8B:
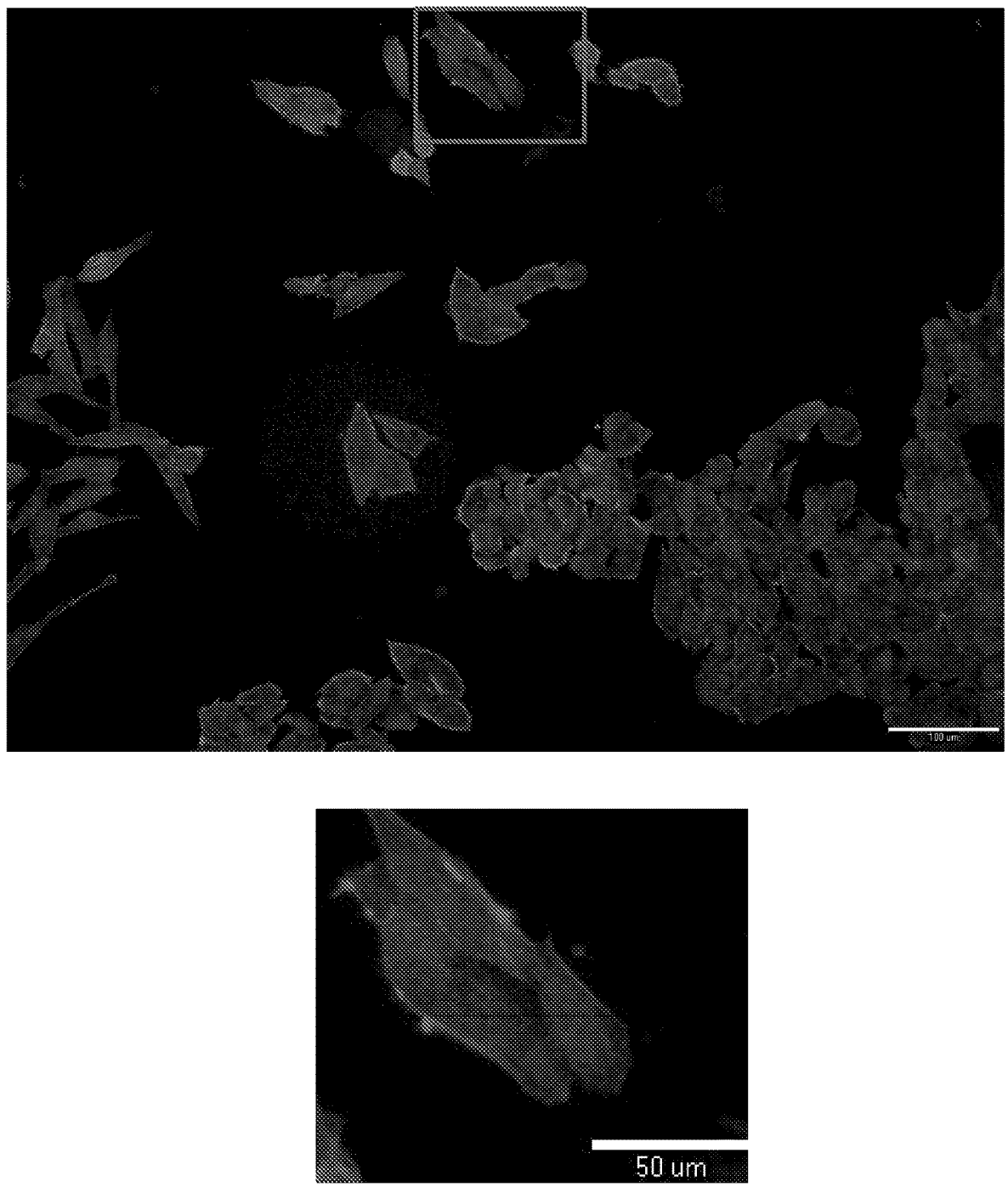
Figure 8C:
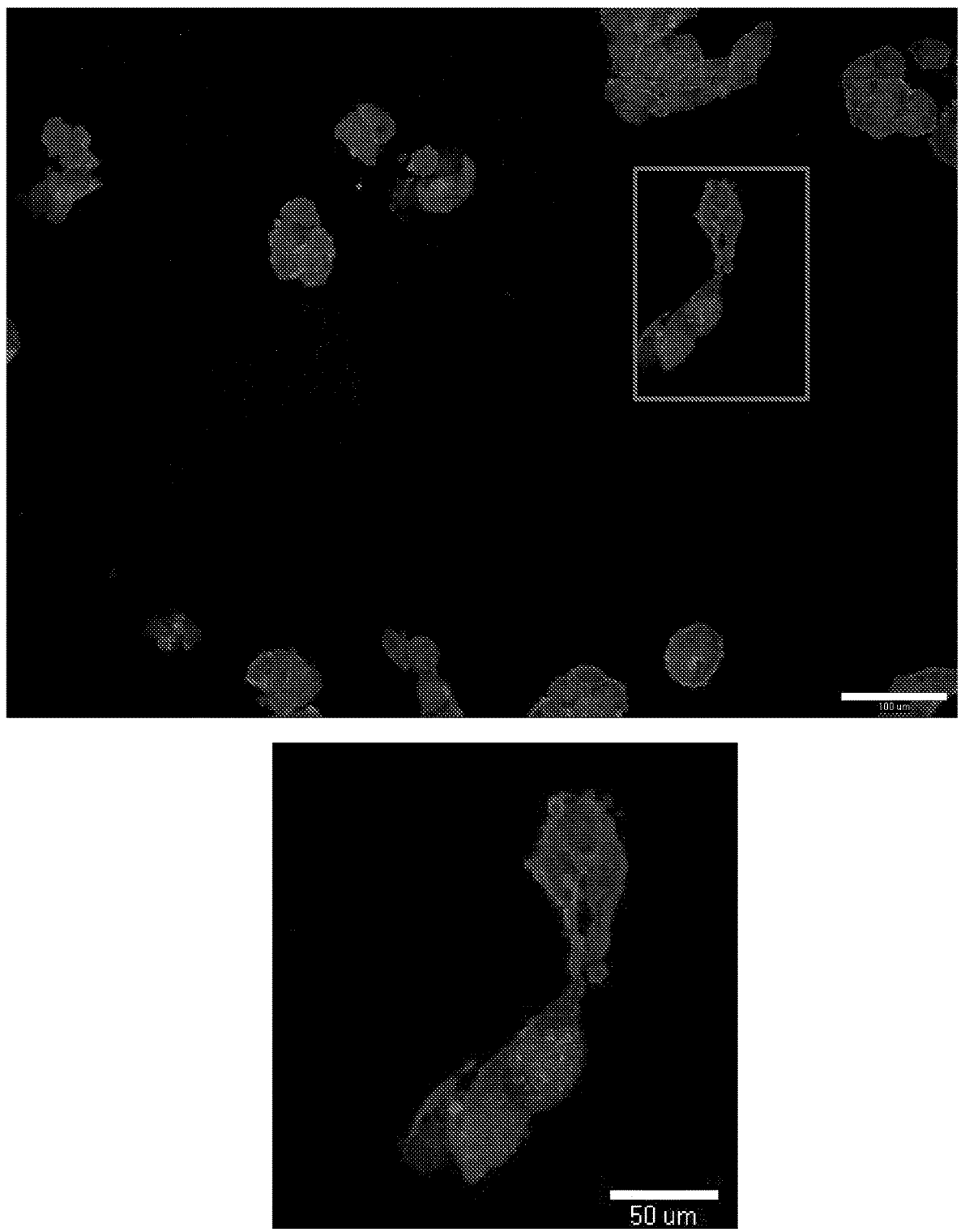

Changes in actin organization were investigated using Alexa Fluor 488 phalloidin (Molecular Probes). Treated-cells were fixed in a solution of 4% paraformaldehyde for 15 min. After rinsing twice with DPBS, the cells were permeabilized with a 0.1% Triton X-100 solution (Sigma-Aldrich) at 4° C. for 10 min, followed by incubation with 3 U/mL phalloidin in DPBS for 30 min. After washing with DPBS, cell nuclei were stained with 300 nM DAPI. The plates were then washed twice with DPBS and analyzed using ImageXpress. Nine sites per well and three wells per treatment were acquired. Results are shown in FIG. 8A (50 µM 7-KC in B16 F10 cells), FIG. 8B (50 µM (3β,5α,6α)-3-Hydroxy-5,6-epoxycholestan-7-one in B16 F10 cells), and FIG. 8C (50 µM 7 oxocholest-5-en-3-beta-yl acetate in B16 F10 cells).

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

The invention claimed is:

1. A method of therapeutically treating cancer, wherein the cancer is melanoma, cervical cancer, breast cancer, liver cancer, lung cancer, brain cancer, leukemia, or prostate cancer, the method comprising administering an emulsion or a lipoprotein-like particle comprising 7-ketocholesterol; cholestane-3α-5β-6α-triol; 3,5-cholestadien-7-one; (3β,5α,6α)-cholestane-3,6-diol; cholesteryl acetate; 7-oxocholest-5-en-3-beta-yl acetate; 5β-6β-epoxy-cholesterol; or (3β,5α,6α)-3-hydroxy-5,6-epoxycholestan-7-one to a subject in need thereof.

2. The method of claim 1, wherein the emulsion is a microemulsion.

3. The method of claim 1, wherein the emulsion is a nanoemulsion.

4. The method of claim 1, wherein the lipoprotein-like particle carries an agent.

5. The method of claim 4, wherein the agent is a cancer therapeutic.

6. The method of claim 4, wherein the compound and the agent exert a synergistic effect against the cancer.

\* \* \* \* \*